United States Patent
Lagu et al.

(10) Patent No.: US 11,912,681 B2
(45) Date of Patent: Feb. 27, 2024

(54) CRYSTALLINE AND SALT FORMS OF PPAR AGONIST COMPOUNDS

(71) Applicant: Mitobridge, Inc., Cambridge, MA (US)

(72) Inventors: Bharat Lagu, Acton, MA (US); Scott Trzaska, Raritan, NJ (US)

(73) Assignee: Mitobridge, Inc., Cambridge, MA (US)

( * ) Notice: Subject to any disclaimer, the term of this patent is extended or adjusted under 35 U.S.C. 154(b) by 0 days.

(21) Appl. No.: 18/082,847

(22) Filed: Dec. 16, 2022

(65) Prior Publication Data

US 2023/0257360 A1    Aug. 17, 2023

Related U.S. Application Data

(63) Continuation of application No. 17/179,604, filed on Feb. 19, 2021, now Pat. No. 11,530,192, which is a continuation of application No. 16/334,746, filed as application No. PCT/US2017/055403 on Oct. 5, 2017, now Pat. No. 10,927,094.

(60) Provisional application No. 62/404,474, filed on Oct. 5, 2016.

(51) Int. Cl.
| | |
|---|---|
| *C07D 401/04* | (2006.01) |
| *C07D 233/60* | (2006.01) |
| *C07D 233/64* | (2006.01) |

(52) U.S. Cl.
CPC ......... *C07D 401/04* (2013.01); *C07D 233/60* (2013.01); *C07D 233/64* (2013.01); *C07B 2200/13* (2013.01)

(58) Field of Classification Search
CPC .................................................. C07D 401/04
See application file for complete search history.

(56) References Cited

U.S. PATENT DOCUMENTS

| | | |
|---|---|---|
| 7,906,657 B2 | 3/2011 | Eggenweiler et al. |
| 10,399,958 B2 | 9/2019 | Downes et al. |
| 10,479,775 B1 | 11/2019 | Downes et al. |
| 10,927,094 B2 | 2/2021 | Lagu et al. |
| 11,530,192 B2 | 12/2022 | Lagu et al. |
| 11,578,052 B2 | 2/2023 | Downes et al. |
| 2020/0181108 A1 | 6/2020 | Lagu et al. |
| 2021/0171494 A1 | 6/2021 | Lagu et al. |

FOREIGN PATENT DOCUMENTS

| | | |
|---|---|---|
| CN | 101072557 A | 11/2007 |
| CN | 101141957 A | 3/2008 |
| CN | 101296892 A | 10/2008 |
| CN | 102300847 A | 12/2011 |
| CN | 102727489 A | 10/2012 |
| CO | 2018004473 A2 | 9/2018 |
| EA | 200802223 A1 | 6/2009 |
| JP | 2018-534355 A | 11/2018 |
| JP | 2019-511527 A | 4/2019 |
| JP | 2019-533660 A | 11/2019 |
| KR | 20180095797 A | 8/2018 |
| TW | 201722919 A | 7/2017 |
| WO | 2004/063166 A1 | 7/2004 |
| WO | 2006/063715 A1 | 6/2006 |
| WO | 2006/084176 A2 | 8/2006 |
| WO | 2007/134677 A1 | 11/2007 |
| WO | 2010/073235 A1 | 7/2010 |
| WO | 2016/057658 A1 | 4/2016 |
| WO | 2017/062468 A1 | 4/2017 |
| WO | 2017/180818 A1 | 10/2017 |
| WO | 2018/067857 A1 | 4/2018 |

OTHER PUBLICATIONS

Berge et al., Pharmaceutical salts. J Pharm Sci. Jan. 1977;66(1):1-19.
International Search Report and Written Opinion for Application No. PCT/US2017/055403, dated Nov. 23, 2017, 9 pages.

*Primary Examiner* — Laura L Stockton

(74) *Attorney, Agent, or Firm* — McCarter & English, LLP; Wei Song; James M. Alburger

(57) ABSTRACT

This disclosure relates to salt forms of compounds capable of activating PPARδ for use in drug substance and drug product development, and related compositions and methods.

9 Claims, 2 Drawing Sheets

CRYSTALLINE AND SALT FORMS OF PPAR AGONIST COMPOUNDS

CROSS-REFERENCE TO RELATED APPLICATIONS

This application is a continuation application of U.S. patent application Ser. No. 17/179,604, filed on Feb. 19, 2021, which is a continuation application of U.S. application Ser. No. 16/334,746, filed on Mar. 19, 2020, now U.S. Pat. No. 10,927,094, which is U.S. national stage filing, under 35 U.S.C. § 371(c), of International Application No. PCT/US2017/055403, filed on Oct. 5, 2017, which claims the benefit of U.S. Provisional Application No. 62/404,474, filed on Oct. 5, 2016. The entire teachings of the aforementioned applications are incorporated herein by reference.

FIELD OF THE INVENTION

This disclosure relates to solid forms of compounds capable of activating PPARδ for use in drug substance and drug product development, and related compositions and methods.

BACKGROUND OF THE INVENTION

Peroxisome proliferator-activated receptor delta (PPARδ) is a nuclear receptor that is capable of regulating mitochondria biosynthesis. As shown in PCT/2014/033088, incorporated herein by reference, modulating the activity of PPARδ is useful for the treatment of diseases, developmental delays, and symptoms related to mitochondrial dysfunction, such as Alpers Disease, MERRF-Myoclonic epilepsy and ragged-red fiber disease, Pearson Syndrome, and the like. Modulation PPARδ activity is effective in the treatment of other conditions, such as muscular diseases, demyelinating diseases, vascular diseases, and metabolic diseases. Indeed, PPARδ is an important biological target for compounds used to help treat and prevent mitochondrial diseases, muscle-related diseases and disorders, and other related conditions.

Compound A of Formula (I) and Compound B of Formula (II) are PPARδ agonists. There is a need for salt forms of these compounds that are crystalline and otherwise have physical properties that are amenable to large scale manufacture. There is also a need for pharmaceutical formulations in which these drug candidates are stable and are effectively delivered to the patient.

SUMMARY OF THE INVENTION

Provided herein, inter alia, are salts of Compound A and Compound B and compositions comprising such compounds that are useful for increasing PPARδ activity.

In one embodiment, provided herein is Compound A of the Formula (I):

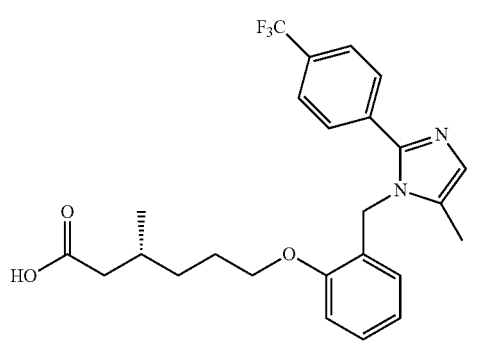

(I)

in the form of a hemisulfate salt. In one embodiment, the hemisulfate salt of Compound A is crystalline. Thus, in one embodiment, the crystalline the hemisulfate salt of Compound A is characterized by an X-ray powder diffraction pattern substantially in accordance with FIG. 1 or FIG. 2.

In another embodiment, provided herein is Compound B of the Formula (II):

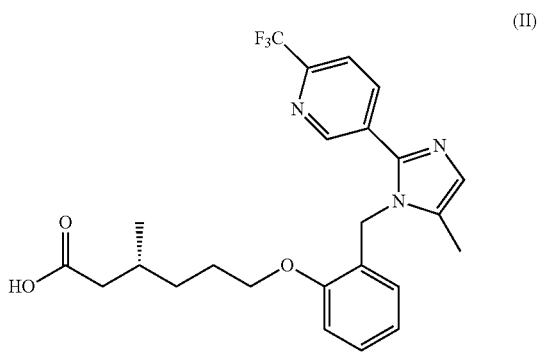 [SMILES: Cc1cnc(-c2ccc(C(F)(F)F)nc2)n1Cc1ccccc1OCCC[C@@H](C)CC(=O)O]

(II)

in the form of a meglumine salt or a hydrated form of the meglumine salt.

Pharmaceutical compositions of the salts of Compound A and Compound B also are disclosed herein. Particular embodiments comprise a pharmaceutically acceptable carrier or excipient and one or more of the disclosed compounds. The pharmaceutical compositions of the invention can be used in therapy, e.g., for treating a PPARδ-related disease or condition in a subject.

Another embodiment comprises treating a PPARδ-related disease or condition in a subject by administering to the subject a therapeutically effective amount of one or both of the disclosed compounds, or a pharmaceutical composition comprising the compound(s).

Also provided herein is the use of one or more of the disclosed compounds, or a pharmaceutical composition comprising one or both of the disclosed compounds, for the preparation of a medicament for the treatment of a PPARδ-related disease or condition.

In another embodiment provided herein, the disclosed compounds or a pharmaceutical composition comprising one or both of the disclosed compounds are for use in treating a PPARδ-related disease or condition.

DETAILED DESCRIPTION OF THE INVENTION

Figure 1:
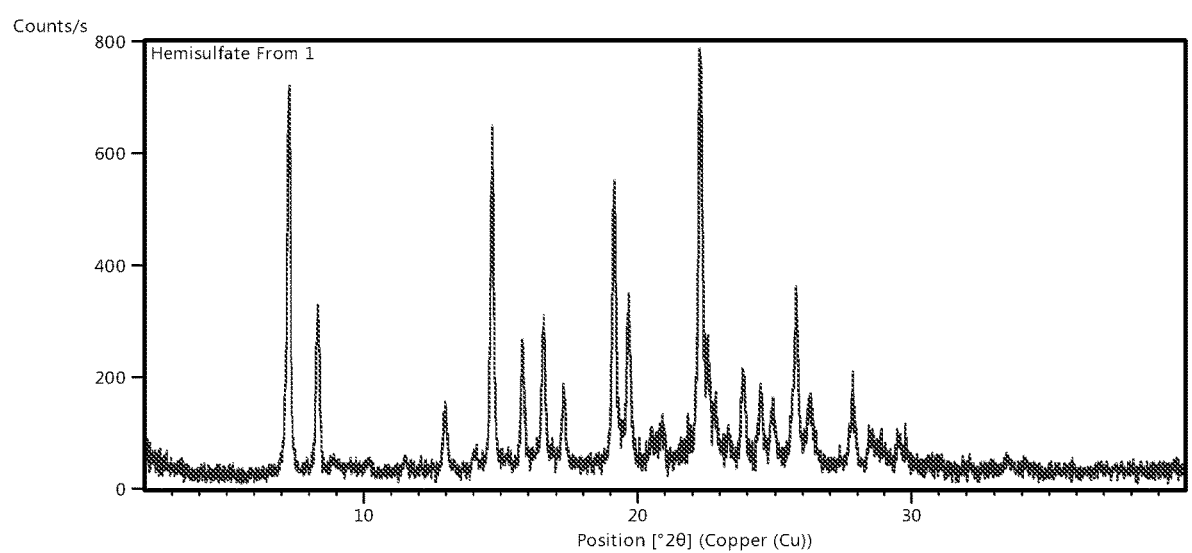
FIG. 1 depicts the X-ray powder diffraction pattern of Compound A hemisulfate form 1.

Peroxisome proliferator-activated receptor delta (PPAR-δ), also known as peroxisome proliferator-activated receptor beta (PPAR-β) or as NR1C2 (nuclear receptor subfamily 1, group C, member 2), refers to a nuclear receptor protein that functions as a transcription factor regulating the expression of genes. PPARS (OMIM 600409) sequences are publically available, for example from GenBank® sequence database (e.g., accession numbers NP_001165289.1 (human, protein)

NP_035275 (mouse, protein), NM_001171818 (human, nucleic acid) and NM_011145 (mouse, nucleic acid)).

Ligands of PPARδ, such as Compound A and Compound B, can promote myoblast proliferation after injury, such as injury to skeletal muscle. As such, as shown in PCT/2014/033088, incorporated herein by reference, modulating the activity of PPARδ is useful for the treatment of diseases, developmental delays, and symptoms related to mitochondrial dysfunction, such as Alpers Disease, MERRF-Myoclonic epilepsy and ragged-red fiber disease, Pearson Syndrome, and the like. Modulation PPARδ activity is effective in the treatment of other conditions, such as muscular diseases, demyelinating diseases, vascular diseases, and metabolic diseases. Indeed, PPARδ is an important biological target for compounds used to help treat and prevent mitochondrial diseases, muscle-related diseases and disorders, and other related conditions.

Herein, the phrase "PPARδ agonist" refers to substances that increase the activity of PPARδ. Substances can be tested for their PPARδ agonist activity by contacting the substance with cells expressing PPARδ, detecting their binding with PPARδ and then detecting signals that serve as the indicator of the activation of PPARδ. Example 1a provides an assay showing that Compound A and Compound B activate PPARδ.

Compounds of the Invention

Provided herein is a hemisulfate salt of (R)-3-methyl-6-(2-((5-methyl-2-(4-(trifluoromethyl)phenyl)-1H-imidazol-1-yl)methyl)phenoxy)hexanoic acid, i.e., Compound A of the Formula (I):

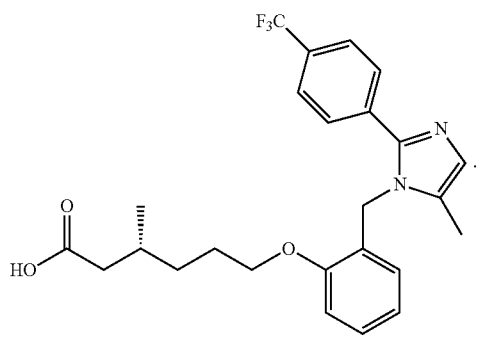

Formula (I)

In some embodiments, the hemisulfate salt of Compound A is crystalline.

Also provided herein are methods of making a hemisulfate salt of Compound A, particularly a crystalline hemisulfate salt of Compound A. For example, upon formation by a reaction between Compound A and sulfuric acid in acetonitrile or 2-propanol, the hemisulfate salt of the compound can be isolated from the reaction mixture by crystallization (see, e.g., Example 3). Accordingly, in one embodiment, provided herein is a method of making the hemisulfate salt of Compound A, the method comprising the step of reacting Compound A, with sulfuric acid in a solvent to form the hemisulfate salt of Compound A. In a particular embodiment, the solvent comprises acetonitrile. Alternatively, the solvent comprises 2-propanol. The synthesis of Compound A is described in Example 2a.

Also provided herein is a meglumine salt of (R)-3-methyl-6-(2-((5-methyl-2-(6-(trifluoromethyl)pyridin-3-yl)-1H-imidazol-1-yl)methyl)phenoxy)hexanoic acid, i.e., Compound B of the Formula (II):

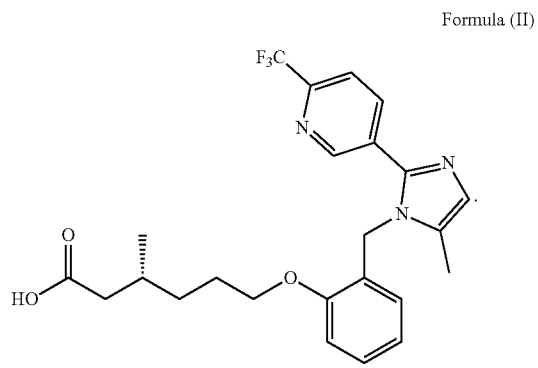 [SMILES: Cc1cnc(-c2ccc(C(F)(F)F)nc2)n1Cc1ccccc1OCCC[C@@H](C)CC(=O)O]

Formula (II)

Compound B may also be provided as a hydrate of the meglumine salt. In a particular embodiment, the meglumine salt of Compound B is provided in monohydrate form, i.e., the meglumine salt of Compound B is complexed with water in a one-to-one molar ratio. In other embodiments, the meglumine salt of Compound B is provided in unhydrated form. The term "unhydrated form" means substantially no water is complexed with the compound, e.g., less than 0.05 equivalents and preferably less than 0.01 equivalents of water relative to the compound.

Also provided are methods of making a meglumine salt of Compound B. For example, upon formation by a reaction between Compound B and meglumine in a solvent such as 2-propanol or acetonitrile, the meglumine salt of Compound B can be isolated from the reaction mixture (see, e.g., Example 11).

Also provided are methods of making a hydrate of the meglumine salt of Compound B. For example, upon formation by a reaction between Compound B and meglumine in an aqueous solvent mixture such as tetrahydrofuan and water, the hydrate of the meglumine salt of Compound B can be isolated from the reaction mixture (see, e.g., Example 12).

The synthesis of Compound B is described in Example 2b.

Polymorphic Forms of the Hemisulfate Salt of Compound A

The hemisulfate salt of Compound A can exist in one of at least two polymorphic forms, i.e., Compound A hemisulfate form 1 and Compound A hemisulfate form 2. Compound A hemisulfate form 1 possesses acceptable crystallinity and melting point (Example 6); stability and hygroscopicity (Example 10); and solubility and form control (Example 7). As shown in Example 10, Compound A hemisulfate form 1 was determined to be more thermodynamically stable than Compound A hemisulfate form 2.

Compound A hemisulfate form 1 is characterized by an X-ray powder diffraction pattern substantially in accordance with FIG. 1. Specifically, Compound A hemisulfate form 1 is characterized by a X-ray powder diffraction pattern comprising one or more characteristic peaks expressed in degrees-2-theta (±0.2) as listed in the Table 3 (Example 6).

In an embodiment, Compound A hemisulfate form 1 is characterized by a first X-ray powder diffraction pattern comprising characteristic peaks expressed in having peaks expressed in degrees-2-theta at angles 7.3±0.2°, 14.7±0.2°, 19.1±0.2°, and 22.3±0.2°. In one embodiment, this first X-ray powder diffraction pattern further comprises characteristic peaks expressed in having peaks expressed in degrees-2-theta one or more of angles 8.3±0.2°, 15.8±0.2°, 16.5±0.2°, 19.7±0.2°, or 25.8±0.2°. In a certain embodiment, this first X-ray powder diffraction pattern comprising characteristic peaks expressed in having peaks expressed in degrees-2-theta at angles 7.3±0.2°, 8.3±0.2°, 14.7±0.2°, 15.8±0.2°, 16.5±0.2°, 19.1±0.2°, 19.7±0.2°, 22.3±0.2°, and 25.8±0.2°.

This first X-ray powder diffraction pattern can also further comprise an X-ray powder diffraction pattern having peaks expressed in degrees-2-theta at one or more of angles 13.0±0.2°, 17.3±0.2°, 23.8±0.2°, 24.5±0.2°, 24.9±0.2°, 26.3±0.2°, or 27.8±0.2°. In a certain embodiment, this first X-ray powder diffraction pattern comprising characteristic peaks expressed in having peaks expressed in degrees-2-theta at angles 7.3±0.2°, 8.3±0.2°, 13.0±0.2°, 14.7±0.2°, 15.8±0.2°, 16.5±0.2°, 17.3±0.2°, 19.1±0.2°, 19.7±0.2°, 22.3±0.2°, 23.8±0.2°, 24.5±0.2°, 24.9±0.2°, 25.8±0.2°, 26.3±0.2°, and 27.8±0.2°.

In a specific embodiment, this first X-ray powder diffraction pattern comprises peaks expressed in degrees-2-theta at angles 7.3±0.2°, 8.3±0.2°, 13.0 0.2°, 14.7±0.2°, 15.8±0.2°, 16.5±0.2°, 17.3±0.2°, 19.2±0.2°, 19.7±0.2°, 20.7±0.2°, 22.3±0.2°, 23.8±0.2°, 24.5±0.2°, 24.9±0.2°, 25.8±0.2°, 26.3±0.2°, 27.8±0.2°, 28.5±0.2°, 29.6±0.2°, and 33.7±0.2°.

Figure 2:
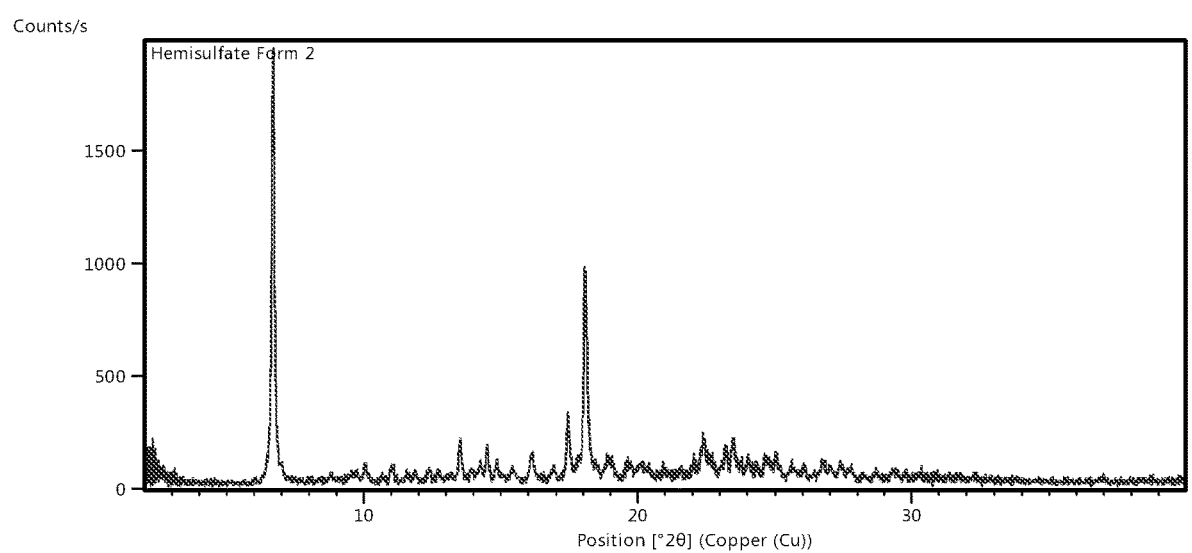
FIG. 2 depicts the X-ray powder diffraction pattern of Compound A hemisulfate form 2.

Compound A hemisulfate form 2 is characterized by an X-ray powder diffraction pattern substantially in accordance with FIG. 2. Specifically, Compound A hemisulfate form 2 is characterized by a X-ray powder diffraction pattern comprising one or more characteristic peaks expressed in degrees-2-theta (±0.2) as listed in the Table 5 (Example 8).

In an embodiment, Compound A hemisulfate form 2 can be characterized by a second X-ray powder diffraction pattern comprising characteristic peaks expressed in having peaks expressed in degrees-2-theta at angles 6.7±0.2°, 13.5±0.2°, 17.4±0.2°, and 18.1±0.2°. In one embodiment, this second X-ray powder diffraction pattern further comprises characteristic peaks expressed in having peaks expressed in degrees-2-theta one or more of angles 14.5±0.2°, 16.±0.2°, 22.4±0.2°, 23.2, or 23.4±0.2°. In a certain embodiment, this second X-ray powder diffraction pattern comprises characteristic peaks expressed in having peaks expressed in degrees-2-theta at angles 6.7±0.2°, 13.5±0.2°, 14.5±0.2°, 16.±0.2°, 17.4±0.2°, 18.1±0.2°, 22.4±0.2°, 23.2, and 23.4±0.2°.

This second X-ray powder diffraction pattern can also further comprise an X-ray powder diffraction pattern having peaks expressed in degrees-2-theta at one or more of angles 10.1±0.2°, 11.1±0.2°, 14.2±0.2°, 14.8±0.2°, 16.9±0.2°, 19.0±0.2°, 25.0±0.2°, 26.8±0.2°, or 27.4±0.2°. In a certain embodiment, this second X-ray powder diffraction pattern comprises characteristic peaks expressed in having peaks expressed in degrees-2-theta at angles 6.7±0.2°, 10.1±0.2°, 11.1±0.2°, 13.5±0.2°, 14.2±0.2°, 14.5±0.2°, 14.8±0.2°, 16.±0.2°, 16.9±0.2°, 17.4±0.2°, 18.1±0.2°, 19.0±0.2°, 22.4±0.2°, 23.2, 23.4±0.2°, 25.0±0.2°, 26.8±0.2°, and 27.4±0.2°.

In a specific embodiment, the second X-ray powder diffraction pattern comprises peaks expressed in degrees-2-theta at angles 6.7±0.2°, 10.1±0.2°, 11.1±0.2°, 13.5±0.2°, 14.2±0.2°, 14.5±0.2°, 14.8±0.2°, 16.1±0.2°, 16.9±0.2°, 17.4±0.2°, 18.1±0.2°, 19.0±0.2°, 19.9±0.2°, 22.4±0.2°, 23.2±0.2°, 23.4±0.2°, 25.0±0.2°, 26.8±0.2°, 27.4±0.2°, and 29.4±0.2°.

In one embodiment, the crystalline hemisulfate salt of Compound A is substantially free from impurities. In another embodiment, the crystalline hemisulfate salt of Compound A comprises less than 10% by weight total impurities. In another embodiment, provided herein is the crystalline hemisulfate salt of Compound A comprises less than 5% by weight total impurities. In another embodiment, the crystalline hemisulfate salt of Compound A comprises less than 1% by weight total impurities. In yet another embodiment, the crystalline hemisulfate salt of Compound A comprises less than 0.1% by weight total impurities.

In certain embodiments, the X-ray powder diffraction pattern of the crystalline hemisulfate salt of Compound A is collected using Cu K alpha (1.5406 Angstrom) radiation.

In another embodiment, provided herein is the crystalline hemisulfate salt of Compound A that is substantially free from amorphous hemisulfate salt of Compound A. As used herein, the term "substantially free from amorphous hemisulfate salt of Compound A" means that the crystalline hemisulfate salt of Compound A contains no significant amount of amorphous hemisulfate salt of Compound A. In certain embodiments, at least about 90% by weight of the crystalline hemisulfate salt of Compound A is free from amorphous hemisulfate salt of Compound A. In other embodiments, at least about 95% by weight of the crystalline hemisulfate salt of Compound A is free from amorphous hemisulfate salt of Compound A. In yet other embodiments, at least about 99% by weight of the crystalline hemisulfate salt of Compound A is free from amorphous hemisulfate salt of Compound A. In still other embodiments, at least about 99.9% by weight of the crystalline hemisulfate salt of Compound A is free from amorphous hemisulfate salt of Compound A.

In another embodiment, provided herein is the crystalline hemisulfate salt of Compound A substantially free from other crystalline forms of hemisulfate salt of Compound A. As used herein, the term "substantially free from other crystalline forms of hemisulfate salt of Compound A" means that the crystalline Compound A contains no significant amount of other crystalline forms of hemisulfate salt of Compound A. In certain embodiments, at least about 90% by weight of the crystalline hemisulfate salt of Compound A is free of other crystalline forms.

In other embodiments, at least about 95% by weight of the crystalline hemisulfate salt of Compound A is free of other crystalline forms. In yet other embodiments, at least about 99% by weight of the crystalline hemisulfate salt of Compound A is free of other crystalline forms. In still other embodiments, at least about 99.9% by weight of the crystalline hemisulfate salt of Compound A is free of other crystalline forms.

Methods of Treatment

Methods of treating a PPARδ-related disease or condition in a subject are disclosed. The methods can include administering to the subject a therapeutically effective amount of one or more compounds or compositions provided herein.

In one embodiment, the PPARδ-related disease is a mitochondrial disease. Examples of mitochondrial diseases include, but are not limited to, Alpers Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome.

In other embodiments, the PPARδ-related disease is a vascular disease (such as a cardiovascular disease or any disease that would benefit from increasing vascularization in tissues exhibiting impaired or inadequate blood flow). In other embodiments, the PPARδ-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the PPARδ-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the PPARδ-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the PPARδ-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the PPARδ-related disease is a neuronal activation disorder, Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the PPARδ-related disease is a muscle fatigue disorder. Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the PPARδ-related disease is a muscle mass disorder. Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the PPARδ-related disease is a beta oxidation disease. Examples of beta oxidation diseases include, but are not limited to, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In some embodiments, the PPARδ-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the PPARδ-related disease is an ocular vascular disease. Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the PPARδ-related disease is a muscular eye disease. Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia.

In yet other embodiments, the PPARδ-related disease is a metabolic disease. Examples of metabolic disorders include, but are not limited to, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the PPARδ-related disease is cancer. Examples of cancer include, but are not limited to, cancers of the colon, large intestine, skin, breast, prostate, ovary, and/or lung.

In other embodiments, the PPARδ-related disease is a renal disease. Examples of renal diseases include, but are not limited to, glomerulonephritis, glomerulosclerosis, nephrotic syndrome, hypertensive nephrosclerosis, acute nephritis, recurrent hematuria, persistent hematuria, chronic nephritis, rapidly progressive nephritis, acute kidney injury (also known as acute renal failure), chronic renal failure, diabetic nephropathy, or Bartter's syndrome. PCT/US2014/033088, incorporated herein by reference, demonstrates genetic and pharmacological activation of PPARδ promotes muscle regeneration in an acute thermal injury mouse model. Accordingly, use of PPARδ as a therapeutic target to enhance regenerative efficiency of skeletal muscle is also provided.

Pharmaceutical Compositions and Administration Thereof

The precise amount of compound administered to provide a "therapeutically effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. The term "therapeutically effective amount" means an amount when administered to the subject which results in beneficial or desired results, including clinical results, e.g., inhibits, suppresses or reduces the symptoms of the condition being treated in the subject as compared to a control. For example, a therapeutically effective amount can be from, e.g., 0.1 mg to about 50 g per day.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Oral and intravenous administration are commonly used, for example, when the condition being treated is acute kidney injury. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

Pharmaceutical compositions are disclosed that include the salts of Compound A and/or Compound B, and typically at least one additional substance, such as an excipient, a known therapeutic other than those of the present disclosure, and combinations thereof.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings.

Administration of therapeutic agents by intravenous formulation is well known in the pharmaceutical industry. Intravenous formulations comprise the pharmaceutically active agent dissolved in a pharmaceutically acceptable solvent or solution, such as sterile water, normal saline solutions, lactated Ringer's, or other salt solutions such as Ringer's solution.

For example, the formulation should promote the overall stability of the active ingredient(s), also, the manufacture of the formulation should be cost-effective. All of these factors ultimately determine the overall success and usefulness of an intravenous formulation.

An oral formulation typically is prepared as a compressed preparation in, for example, the form of a tablet or pill. A tablet may contain, for example, about 5-10% of the active ingredient (e.g., a salt of Compound A or B); about 80% of fillers, disintegrants, lubricants, glidants, and binders; and 10% of compounds which ensure easy disintegration, disaggregation, and dissolution of the tablet in the stomach or the intestine. Pills can be coated with sugar, varnish, or wax to disguise the taste.

EXEMPLIFICATION

Example 1

PPARδ Activity Screen

Cell Culture and Transfection: CV-1 cells were grown in DMEM+10% charcoal stripped FCS. Cells were seeded into 384-well plates the day before transfection to give a confluency of 50-80% at transfection. A total of 0.8 g DNA containing 0.64 micrograms pCMX-PPARDelta LBD, 0.1 micrograms pCMX.beta.Gal, 0.08 micrograms pGLMH2004 reporter and 0.02 micrograms pCMX empty vector was transfected per well using FuGene transfection reagent according to the manufacturer's instructions (Roche). Cells were allowed to express protein for 48 h followed by addition of compound.

Plasmids: Human PPARδ was used to PCR amplify the PPARδ LBD. The amplified cDNA ligand binding domain (LBD) of PPARδ isoform was (PPARδ amino acid 128 to C-terminus) and fused to the DNA binding domain (DBD) of the yeast transcription factor GAL4 by subcloning fragments in frame into the vector pCMX GAL (Sadowski et al. (1992), Gene 118, 137) generating the plasmids pCMX-PPARDelta LBD. Ensuing fusions were verified by sequencing. The pCMXMH2004 luciferase reporter contains multiple copies of the GAL4 DNA response element under a minimal eukaryotic promoter (Hollenberg and Evans, 1988). pCMXPGal was generated.

Compounds: All compounds were dissolved in DMSO and diluted 1:1000 upon addition to the cells. Compounds were tested in quadruple in concentrations ranging from 0.001 to 100 µM. Cells were treated with compound for 24 h followed by luciferase assay. Each compound was tested in at least two separate experiments.

Luciferase assay: Medium including test compound was aspirated and washed with PBS. 50 µl PBS including 1 mM Mg++ and Ca++ were then added to each well. The luciferase assay was performed using the LucLite kit according to the manufacturer's instructions (Packard Instruments). Light emission was quantified by counting on a Perkin Elmer Envision reader. To measure 3-galactosidase activity 25 µl supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods: The activity of a compound is calculated as fold induction compared to an untreated sample. For each compound the efficacy (maximal activity) is given as a relative activity compared to GW501516, a PPARδ agonist. The $EC_{50}$ is the concentration giving 50% of maximal observed activity. $EC_{50}$ values were calculated via non-linear regression using GraphPad PRISM (GraphPad Software, San Diego, Calif.).

TABLE 1

PPARdelta Activity Screen

| Compound | Structure | Mol. Wt | PPAR delta transactivation EC50 (nM) |
|---|---|---|---|
| Compound A | [structure: 4-(trifluoromethyl)phenyl-imidazole with methyl, benzyl-O-linked chain to 3-methyl carboxylic acid] | 460.41 | 0.10 |
| Compound B | [structure: 6-(trifluoromethyl)pyridin-3-yl-imidazole with methyl, benzyl-O-linked chain to 3-methyl carboxylic acid] | 461.49 | 4.40 |

The compounds of this invention show a good agonistic activity of PPARδ, a good selectivity of PPARδ, a good pharmacological effect, good PK profiles and/or low toxicity including CYP inhibition and hERG inhibition.

Example 2

Synthetic Preparation of Compounds A and B

Abbreviations

Me methyl
Et ethyl
nPr n-propyl
iPr isopropyl
cPr cyclopropyl
nBu n-butyl
iBu isobutyl
tBu tert-butyl
Boc tert-butyloxycarbonyl
Ac acetyl
Ph phenyl
Tf trifluoromethanesulfonyl
Ts 4-methylphenylsulfonyl
DIAD diisopropyl azodicarboxylate
EDCI 3-(3-dimethylaminopropyl)-1-ethylcarbodiimide
HOBt 1-hydroxybenzotriazole
HATU 1-[bis(dimethylamino)methylene]-1H-1,2,3-triazolo[4,5-b]pyridinium 3-oxide hexafluorophosphate
HBTU N,N,N',N'-Tetramethyl-O-(1H-benzotriazol-1-yl)uronium hexafluorophosphate
NBS N-bromosuccinimide
DIPEA diisopropylethylamine
mCPBA m-chloroperoxybenzoic acid
Togni's reagent 3,3-dimethyl-1-(trifluoromethyl)-1,2-benziodoxole
DCM dichloromethane
DME dimethoxyethane
DMF N,N-dimethylformamide
DMF·DMA N,N-dimethylformamide dimethyl acetal
DMSO dimethylsulfoxide
TFA trifluoroacetic acid
THF tetrahydrofuran
MW microwave irradiation
aq Aqueous
M concentration expressed in mol/L
RT room temperature
TLC thin layer chromatography
HPLC high-performance liquid chromatography
MPLC medium pressure liquid chromatography
LCMS liquid chromatography-mass spectrometry
ESI+ Electrospray ionization positive mode
ESI− Electrospray ionization negative mode
$^1$H NMR (DMSO-$d_6$) δ (ppm) of peak in H NMR in DMSO-$d_6$
s singlet (spectrum)
d doublet (spectrum)
t triplet (spectrum)
q quartet (spectrum)
dd double doublet (spectrum)
br broad line (spectrum)
m multiplet (spectrum)

Example 2a: Synthesis of (R)-3-methyl-6-(2-((5-methyl-2-(4-(trifluoromethyl)phenyl)-1H-imidazol-1-yl)methyl)phenoxy)hexanoic acid (Compound A)

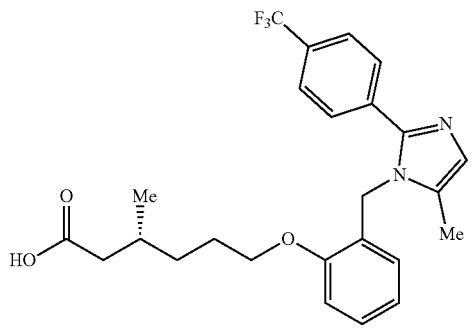 [SMILES: Cc1cnc(-c2ccc(C(F)(F)F)cc2)n1Cc1ccccc1OCCC[C@@H](C)CC(=O)O]

Scheme:

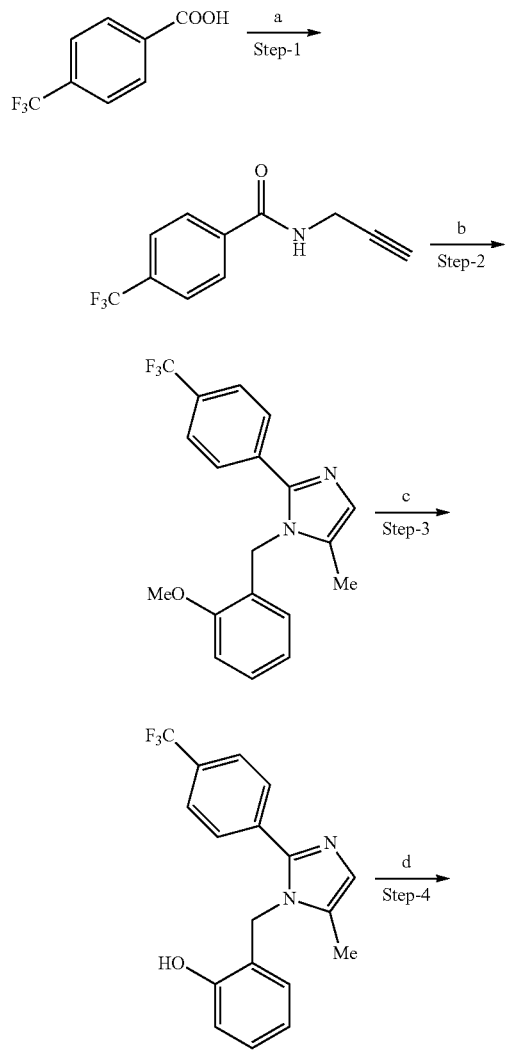

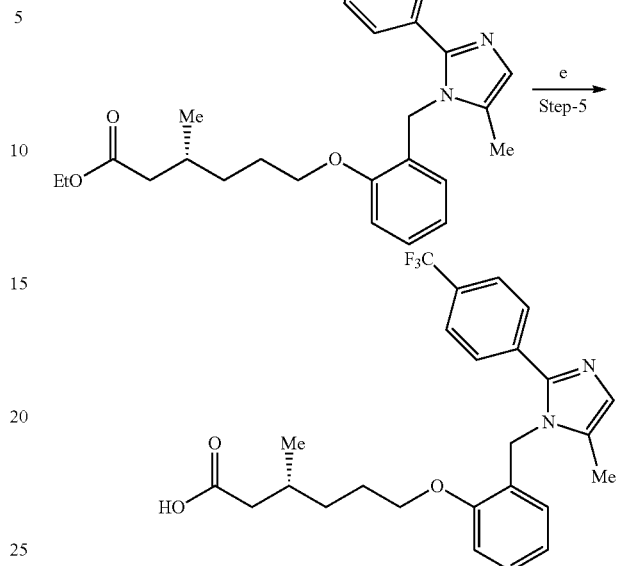

Synthesis of ethyl (R)-6-bromo-3-methylhexanoate

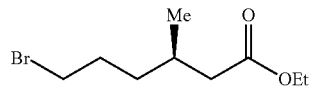 [SMILES: CCOC(=O)C[C@H](C)CCCBr]

In a 1 L round bottom flask, a solution of ethyl (R)-6-hydroxy-3-methylhexanoate (65.0 g, 373.56 mmol) in DCM (650 mL) was treated with PBr$_3$ (101.0 g, 373.56 mmol) at RT. The reaction mixture was stirred at RT for 3 h. Upon completion of reaction (monitored by TLC), the reaction mixture was diluted with water (500 mL) and extracted with diethyl ether (3×500 mL). The organic extract was separated and dried over anhydrous Na$_2$SO$_4$. The solvent was removed under reduced pressure to get the title compound (57.12 g).

Step-1: Synthesis of N-(prop-2-yn-1-yl)-4-(trifluoromethyl)benzamide

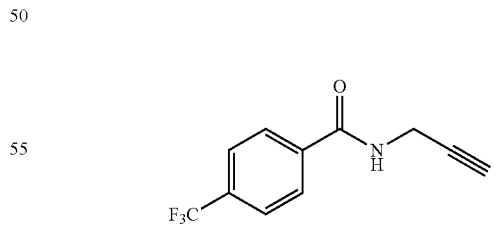

In a 500 mL round bottom flask, a stirred solution of 4-(trifluoromethyl)benzoic acid (10 g, 52.63 mmol) and prop-2-yn-1-amine (3.47 g, 63.15 mmol) in DMF (200 mL) was treated sequentially with EDCI·HCl (20.09 g, 105.2 mmol), HOBt (14.2 g, 105.2 mmol) and Et$_3$N (14.6 mL, 105.2 mmol) at RT under nitrogen atmosphere. The reaction mixture was stirred at RT for 12 h under nitrogen atmosphere. Upon completion of reaction (monitored by TLC), the reaction mixture was diluted with ice cold water and solid precipitated out. The solid was filtered and dried under reduced pressure to yield the title compound (8.42 g, 70.5%).

¹H NMR (300 MHz, CDCl₃): δ 7.90 (d, J=8.1 Hz, 2H), 7.71 (d, J=8.8 Hz, 2H), 6.47 (brs, 1H), 4.28-4.62 (m, 2H), 3.12 (t, J=2.4 Hz, 1H). LCMS (ESI+, m/z): 228.2 (M+H)⁺.

Step-2: Synthesis of 1-(2-methoxybenzyl)-5-methyl-2-(4-(trifluoromethyl)phenyl)-1H-imidazole

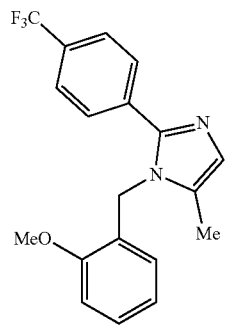 [SMILES: COc1ccccc1Cn1c(C)cnc1-c1ccc(C(F)(F)F)cc1]

In a 500 mL resealable reaction tube, a solution of N-(prop-2-yn-1-yl)-4-(trifluoromethyl)benzamide (13.3 g, 58.59 mmol) and 2-methoxybenzyl amine (12.0 g, 87.84 mmol) in toluene (150 mL) was treated with Zn(OTf)₂ (6.67 g, 17.5 mmol) at RT under nitrogen atmosphere. The reaction mixture was heated at 110° C. for 12 h. Upon completion of reaction (monitored by TLC), the reaction mixture was diluted with water and extracted with EtOAc (3×100 mL). The combined organic extract was washed with saturated NaHCO₃, brine and dried over anhydrous Na₂SO₄. The solution was concentrated under reduced pressure and the residue obtained was purified by silica gel column chromatography (elution, 25% EtOAc in hexanes) to afford the title compound (17.3 g, 85.3%).

¹H NMR (400 MHz, CDCl₃): δ 7.59-7.54 (m, 4H), 7.30-7.23 (m, 1H), 7.00 (s, 1H), 6.91-6.86 (m, 2H), 6.57 (d, J=7.2 Hz, 1H), 5.11 (s, 2H), 3.84 (s, 3H), 2.11 (s, 3H). LCMS (ESI+, m/z): 347.3 (M+H)⁺.

Step-3: Synthesis of 2-((5-methyl-2-(4-(trifluoromethyl)phenyl)-1H-imidazol-1-yl)methyl)phenol

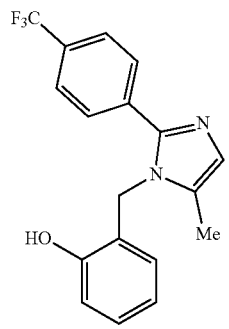

In a 500 mL round bottom flask, a solution of 1-(2-methoxybenzyl)-5-methyl-2-(4-(trifluoromethyl)phenyl)-1H-imidazole (17.3 g, 49.94 mmol) in DCM (150 mL) was treated with BBr₃ (1.0 M, 90.0 mL) drop wise at 0° C. The reaction mixture was stirred at RT for 4 h. Upon completion of reaction (monitored by TLC), the reaction mixture was basified (pH~9) with aqueous NaHCO₃ and extracted with EtOAc (3×500 mL). The combined organic extract was dried over anhydrous Na₂SO₄ and concentrated under reduced pressure to afford the title compound (19.2 g, crude).

¹H NMR (400 MHz, DMSO-d₆): δ 9.99 (s, 1H), 7.88 (d, J=8.4 Hz, 2H), 7.77 (d, J=8.4 Hz, 2H), 7.33 (s, 1H), 7.14-7.10 (m, 1H), 6.83 (d, J=8.0 Hz, 1H), 6.74-6.70 (m, 1H), 6.55 (d, J=6.8 Hz, 1H), 5.21 (s, 2H), 2.16 (s, 3H). LCMS (ESI+, m/z): 333.3 (M+H)⁺.

Step-4: Synthesis of ethyl (R)-3-methyl-6-(2-((5-methyl-2-(4-(trifluoromethyl)phenyl)-1H-imidazol-1-yl)methyl)phenoxy)hexanoate

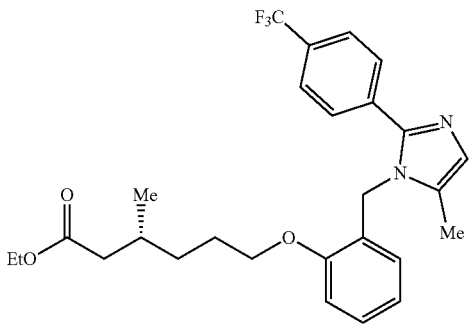 [SMILES: CCOC(=O)C[C@H](C)CCCOc1ccccc1Cn1c(C)cnc1-c1ccc(C(F)(F)F)cc1]

In a 250 mL round bottom flask, a stirred solution of 2-((5-methyl-2-(4-(trifluoromethyl) phenyl)-1H-imidazol-1-yl)methyl)phenol (4.0 g, 12.0 mmol) in DMF (100 mL) was treated with KOᵗBu (4.03 g, 36.1 mmol) and ethyl (R)-6-bromo-3-methylhexanoate (8.52 g, 36.10 mmol) at RT under nitrogen atmosphere. The resulting reaction mixture was stirred at RT for 12 h. Upon completion of the reaction (monitored by TLC), the reaction mixture quenched with ice cold water and extracted with EtOAc (3×100 mL). The combined organic extract was washed with brine, dried over anhydrous Na₂SO₄ and concentrated under reduced pressure. The residue obtained was purified by silica gel column chromatography (gradient elution, 15-30% EtOAc in hexanes) to afford the title compound (3.31 g, 56.3%). LCMS (ESI+, m/z): 489.3 (M+H)⁺.

Step-5: Synthesis of (R)-3-methyl-6-(2-((5-methyl-2-(4-(trifluoromethyl)phenyl)-1H-imidazol-1-yl)methyl)phenoxy)hexanoic acid (Compound A)

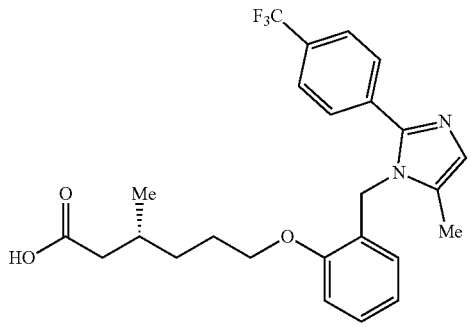

In a 250 mL round bottom flask, a stirred solution of ethyl (R)-3-methyl-6-(2-((5-methyl-2-(4-(trifluoromethyl)phenyl)-1H-imidazol-1-yl)methyl)phenoxy)hexanoate (3.3 g, 6.75 mmol) in THF (30 mL), ethanol (10 mL) and water (10 mL) was treated with lithium hydroxide monohydrate (1.42 g, 33.8 mmol) at RT. The reaction mixture was stirred at RT for 12 h. Upon completion of reaction (monitored by TLC), the reaction mixture was concentrated under reduced pressure. The residue obtained was washed with EtOAc, diluted with cold water and acidified (pH~5) with 1N HCl. The solid obtained was filtered and dried under reduced pressure to give the title compound (1.12 g, 36.0%).

$^1$H NMR (400 MHz, DMSO-d$_6$): δ 12.00 (brs, 1H), 7.71 (d, J=8.4 Hz, 2H), 7.62 (d, J=8.4 Hz, 2H), 7.26-7.21 (m, 1H), 7.01 (d, J=8.4 Hz, 1H), 6.93 (s, 1H), 6.86-6.83 (m, 1H), 6.38 (d, J=6.8 Hz, 1H), 5.16 (s, 2H), 3.98 (t, J=6.0 Hz, 2H), 2.19-2.14 (m, 1H), 2.08 (s, 3H), 1.99-1.93 (m, 1H), 1.84-1.76 (m, 1H), 1.67-1.65 (m, 2H), 1.45-1.42 (m, 1H), 1.28-1.18 (m, 1H), 0.83 (d, J=6.4 Hz, 3H). $^{19}$F NMR (400 MHz, DMSO-d$_6$): δ −56.4. LCMS (ESI+, m/z): 460.8 (M+H)$^+$. HPLC: 98.89% (210 nm).

Example 2b: Synthesis of (R)-3-methyl-6-(2-((5-methyl-2-(6-(trifluoromethyl)pyridin-3-yl)-1H-imidazol-1-yl)methyl)phenoxy)hexanoic acid (Compound B)

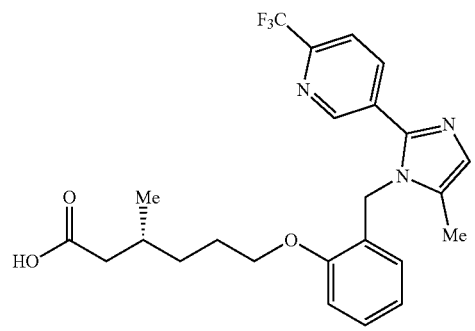 [SMILES: Cc1cnc(-c2ccc(C(F)(F)F)nc2)n1Cc1ccccc1OCCC[C@@H](C)CC(=O)O]

Scheme:

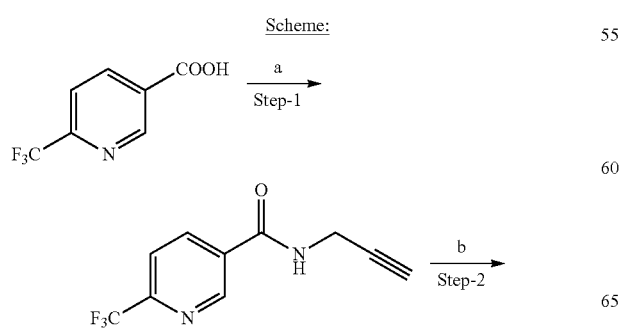

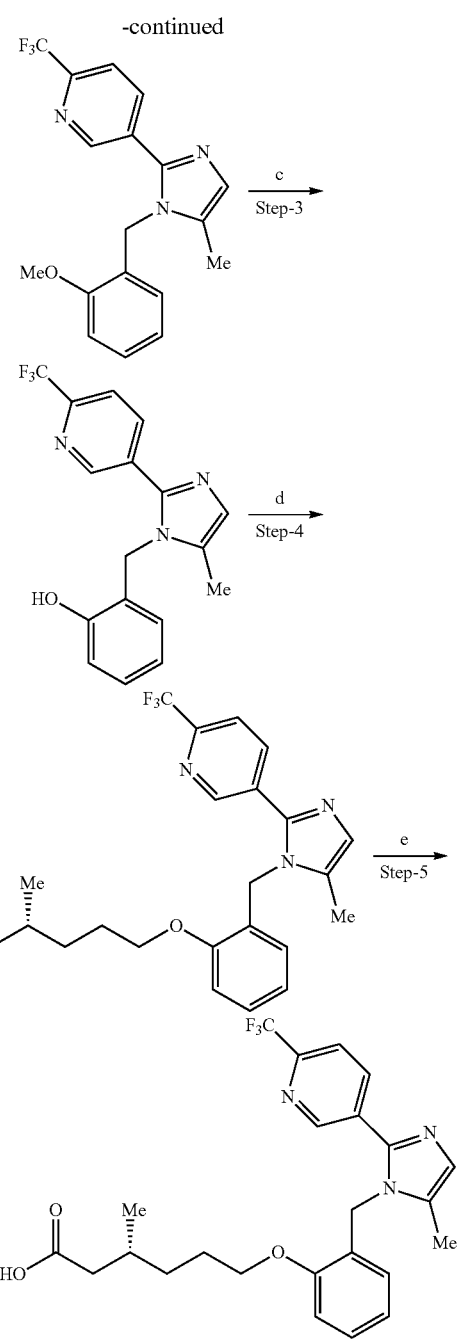

Step-1: Synthesis of N-(prop-2-yn-1-yl)-6-(trifluoromethyl)nicotinamide

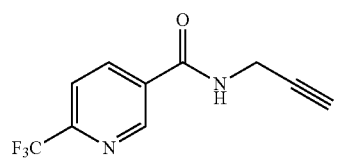 [SMILES: C#CCNC(=O)c1ccc(C(F)(F)F)nc1]

In a 100 mL round bottom flask, a stirred solution of 6-(trifluoromethyl)nicotinic acid (3 g, 15.70 mmol) and prop-2-yn-1-amine (1.05 g, 18.84 mmol) in DMF (50 mL) was treated with HATU (7.2 g, 18.84 mmol) and Et₃N (3.1 mL, 23.55 mmol) at RT under nitrogen atmosphere. The resulting reaction mixture was stirred at RT for 3 h. Upon completion of reaction (monitored by TLC), the reaction mixture was diluted with cold water and solid precipitated was filtered, washed with water and dried under reduced pressure to get the title compound (2.6 g, 72.6%).

$^1$H NMR (300 MHz, CDCl₃): δ 9.08 (d, J=2.1 Hz, 1H), 8.32 (dd, J=8.4, 2.4 Hz, 1H), 7.78 (d, J=7.8 Hz, 1H), 6.62 (brs, 1H), 4.30-4.28 (m, 2H), 2.33 (t, J=2.4 Hz, 1H).

LCMS (ESI+, m/z): 229.2 (M+H)⁺.

Step-2: Synthesis of 5-(1-(2-methoxybenzyl)-5-methyl-1H-imidazol-2-yl)-2-(trifluoromethyl) pyridine

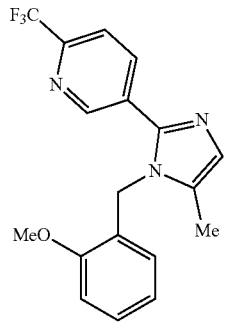 [SMILES: COc1ccccc1Cn1c(C)cnc1-c1ccc(C(F)(F)F)nc1]

In a 50 mL resealable tube, a solution of N-(prop-2-yn-1-yl)-6-(trifluoromethyl) nicotinamide (1.0 g, 4.38 mmol) and 2-methoxyphenybenzyl amine (1.2 g, 8.77 mmol) in toluene (10 mL) was treated with Zn(OTf)₂ (0.16 g, 0.43 mmol) at RT under nitrogen atmosphere. The reaction mixture was heated at 120° C. for 12 h. Upon completion of reaction (monitored by TLC), the reaction mixture was diluted with water and extracted with EtOAc (3×20 mL). The organic extract was washed with saturated NaHCO₃, brine and dried over anhydrous Na₂SO₄. The solution was concentrated under reduced pressure and residue obtained was purified by silica gel column chromatography (elution, 25% EtOAc in hexanes) to yield the title compound (0.8 g, 52.6%).

$^1$H NMR (400 MHz, CDCl₃): δ 8.79 (s, 1H), 8.07 (d, J=8.1 Hz, 1H), 7.68 (d, J=8.1 Hz, 1H), 7.31 (t, J=8.4 Hz, 1H), 7.09 (s, 1H), 6.94-6.87 (m, 2H), 6.56 (d, J=7.5 Hz, 1H), 5.16 (s, 2H), 3.87 (s, 3H). LCMS (ESI+, m/z): 348.3 (M+H)⁺.

Step-3: Synthesis of 2-((5-methyl-2-(6-(trifluoromethyl)pyridin-3-yl)-1H-imidazol-1-yl) methyl)phenol

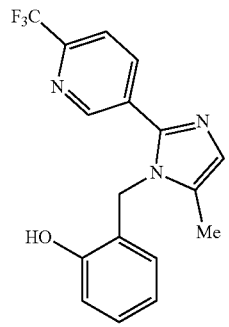 [SMILES: Cc1cnc(-c2ccc(C(F)(F)F)nc2)n1Cc1ccccc1O]

In a 100 mL round bottom flask, a solution of 5-(1-(2-methoxybenzyl)-5-methyl-1H-imidazol-2-yl)-2-(trifluoromethyl)pyridine (0.8 g, 2.31 mmol) in dichloromethane (300 mL) was treated with BBr₃ (0.8 mL, 2.31 mmol) drop wise at 0° C. The reaction mixture was stirred at RT for 2 h. Upon completion of reaction (monitored by TLC), the reaction mixture was basified (pH~9) with aqueous NaHCO₃ and extracted with EtOAc. The organic extract was dried over anhydrous Na₂SO₄ and concentrated under reduced pressure to afford the title compound (0.5 g, 65.1%)

$^1$H NMR (400 MHz, DMSO-d₆): δ 9.92 (s, 1H), 8.83 (s, 1H), 8.12 (d, J=8.1 Hz, 1H), 7.94 (d, J=8.1 Hz, 1H), 7.12 (d, J=6.9 Hz, 1H), 7.02 (s, 1H), 6.87 (d, J=7.8 Hz 1H), 6.73 (t, J=7.2 Hz, 1H), 6.37 (d, J=7.2 Hz, 1H), 5.20 (s, 2H), 2.15 (s, 3H). LCMS (ESI+, m/z): 334.3 (M+H)⁺.

Step-4: Synthesis of ethyl (R)-3-methyl-6-(2-((5-methyl-2-(6-(trifluoromethyl)pyridin-3-yl)-1H-imidazol-1-yl)methyl)phenoxy)hexanoate

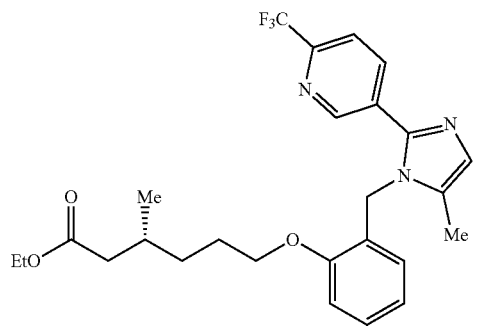 [SMILES: CCOC(=O)C[C@H](C)CCCOc1ccccc1Cn1c(C)cnc1-c1ccc(C(F)(F)F)nc1]

In a 50 mL round bottom flask, a stirred solution of 2-((5-methyl-2-(6-(trifluoromethyl)pyridin-3-yl)-1H-imidazol-1-yl)methyl)phenol (0.5 g, 1.50 mmol) (a procedure for the preparation of which is disclosed in U.S. Application No. 62/061,483, incorporated herein by reference) in DMF (10 mL) was treated with K₂CO₃ (0.41 g, 3.00 mmol) and ethyl (R)-6-bromo-3-methylhexanoate (0.710 g, 3.00 mmol) at RT under nitrogen atmosphere. The resulting reaction mixture was heated 60° C. for 12 h. Upon completion of the reaction (monitored by TLC), the reaction mixture was quenched with ice cold water and extracted with ethyl acetate (75 mL×3). The combined organic extract was washed with brine, dried over anhydrous Na₂SO₄ and concentrated under reduced pressure. The residue obtained was purified by silica gel column chromatography (gradient elution, 15-30% EtOAc in hexanes) to afford the title compound (0.45 g, 61.3%).

LCMS (ESI+, m/z): 491.0 (M+H)+.

Step-5: Synthesis of (R)-3-methyl-6-(2-((5-methyl-2-(6-(trifluoromethyl)pyridin-3-yl)-1H-imidazol-1-yl)methyl)phenoxy)hexanoic acid (Compound B)

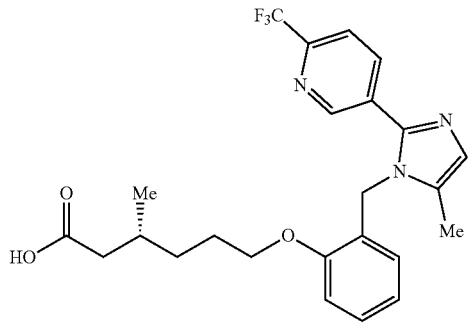 [SMILES: Cc1cnc(-c2ccc(C(F)(F)F)nc2)n1Cc1ccccc1OCCC[C@@H](C)CC(=O)O]

In a 250 mL round bottom flask, a stirred solution of ethyl (R)-3-methyl-6-(2-((5-methyl-2-(6-(trifluoromethyl)pyridin-3-yl)-1H-imidazol-1-yl)methyl)phenoxy)hexanoate (0.45 g, 0.92 mmol) in THF (5 mL), ethanol (2.5 mL) and water (2.5 mL) was treated with lithium hydroxide monohydrate (16.0 g, 74.33 mmol) at RT. The reaction mixture was stirred at RT for 12 h. Upon completion of reaction (monitored by TLC), the reaction mixture was concentrated under reduced pressure. The residue obtained was washed with EtOAc, diluted with cold water and acidified (pH~5) with 1N HCl. The solid was filtered and dried under reduced pressure to give the title compound (0.166 g, 39.2%).

$^1$H NMR (400 MHz, DMSO-$d_6$): δ11.96 (brs, 1H), 8.79 (s, 1H), 8.05 (d, J=8.0 Hz, 1H), 7.90 (d, J=8.0 Hz, 1H), 7.24 (t, J=7.6 Hz, 1H), 7.02 (d, J=8.4 Hz, 1H), 7.00 (s, 1H), 6.84 (t, J=7.6 Hz, 1H), 6.43 (d, J=7.2 Hz, 1H), 5.21 (s, 2H), 3.98 (t, J=6.0 Hz, 2H), 2.19-2.14 (m, 1H), 2.13 (s, 3H), 2.03-1.94 (m, 1H), 1.85-1.80 (m, 1H), 1.68-1.66 (m, 2H), 1.38-1.36 (m, 1H), 1.28-1.18 (m, 1H), 0.85 (d, J=6.4 Hz, 3H). $^{19}$F NMR (400 MHz, DMSO-$d_6$): δ −66.46.

LCMS (ESI+, m/z): 462.3 (M+H)+. HPLC: 95.11% (210 nm).

Example 3

Compound A Salt Screen

A 25 mg/mL stock solution of Compound A was prepared in methanol. Then, 2 mL of Compound A stock solution was dispensed into 4 mL amber glass vials. Salt formers (1 eq) were then added to the vials as listed in Table 1 and the solvents were removed by evaporation under a stream of nitrogen. Once evaporation was completed, the screening solvents listed in Table 1 were pipetted in, the vials were sealed, and the samples were put onto a 50° C. stir plate to stir for up to an hour. Then, the heat was shut off and samples were allowed to cool to 25° C. with stirring. Experiments resulting in slurries were stirred. Experiments resulting in solutions were converted to evaporative crystallizations.

Solids isolated from the experiments were characterized by XRPD to determine if they were crystalline as well as unique solid state forms suggesting salt formation occurred.

An additional experiment was performed with the suspected sodium salt in an attempt to create a Compound A sodium salt. The suspected sodium salt isolated from acetonitrile was slurried in ethyl acetate for six days at 25° C. Solids were analyzed by XRPD, which showed a physical mixture of Compound A free form and the starting suspected sodium salt isolated from acetonitrile. No new salt form was generated.

TABLE 1

Salt Screening Experiments for Compound A

| Sample | Salt Former | Solvent | Temperature | Results |
|---|---|---|---|---|
| 1 | HCl | 2-Propanol | 25° C. | Gel |
| 2 | H2SO4 | 2-Propanol | 25° C. | New Salt Form A (Hemisulfate Form 1) |
| 3 | H3PO4 | 2-Propanol | 25° C. | New Salt Form B |
| 4 | p-Toluenesulfonic Acid | 2-Propanol | 25° C. | Gel |
| 5 | Methanesulfonic Acid | 2-Propanol | 25° C. | Gel |
| 6 | NaOH | 2-Propanol | 25° C. | New Salt Form C |
| 7 | KOH | 2-Propanol | 25° C. | Gel |
| 8 | Choline Hydroxide | 2-Propanol | 25° C. | New Salt Form D |
| 9 | L-Arginine | 2-Propanol | 25° C. | Amorphous |
| 10 | L-Lysine | 2-Propanol | 25° C. | New Salt Form E |
| 11 | N-Methyl-D-Glucamine | 2-Propanol | 25° C. | Gel |
| 12 | TRIS | 2-Propanol | 25° C. | New Salt Form F |
| 13 | HCl | Acetonitrile | 25° C. | Gel |
| 14 | H2SO4 | Acetonitrile | 4° C. | New Salt Form A (Hemisulfate Form 1) |
| 15 | H3PO4 | Acetonitrile | 25° C. | New Salt Form B |
| 16 | p-Toluenesulfonic Acid | Acetonitrile | 25° C. | Gel |
| 17 | Methanesulfonic Acid | Acetonitrile | 25° C. | Gel |
| 18 | NaOH | Acetonitrile | 25° C. | New Salt Form C |
| 19 | KOH | Acetonitrile | 25° C. | Semi-Crystalline |
| 20 | Choline Hydroxide | Acetonitrile | 25° C. | New Salt Form D |
| 21 | L-Arginine | Acetonitrile | 25° C. | Amorphous |
| 22 | L-Lysine | Acetonitrile | 25° C. | New Salt Form E |
| 23 | N-Methyl-D-Glucamine | Acetonitrile | 25° C. | Mixture of Starting Material |
| 24 | TRIS | Acetonitrile | 4° C. | Starting Material |

Example 4

Stability of Compound A Salts

The stability of the sulfate, phosphate, L-lysine, and TRIS salts prepared in Example 3 were tested. Approximately 20 mg of each sample was combined with 1 mL of water in microcentrifuge tubes. The samples were allowed to mix overnight on a temperature controlled shaker at 20° C. at 850 rpm. The solids were characterized by XPRD to determine if a solid state form change occurred. There was no change in the solids for the suspected sulfate salt as well as the starting material. However, the suspected phosphate, L-lysine, and TRIS salts appear to disproportionate back to the starting material in aqueous environments.

Example 5

Preparation of Compound A Hemisulfate Form 1

In a 50 mL vial was dissolved 883.2 mg of Compound A was dissolved in 35 mL methanol. Then, $H_2SO_4$ (1920 µL, 1M in $H_2O$, 1 equivalent) was pipetted in. The solvent was allowed to evaporate under $N_2$. Once evaporated, 2-propanol (18 mL) was pipetted in followed by a stir bar. The vial was capped and placed on a 50° C. stir plate for 1 hour, then the temperature was dropped to 25° C., where it stirred for 1 day. After 1 day, the solids were filtered under vacuum and allowed to air dry.

$^1$H NMR (400 MHz, DMSO-$d_6$): δ 7.85 (d, J=8.4 Hz, 2H), 7.74 (d, J=8.4 Hz, 2H), 7.36 (s, 1H), 7.27 (t, J=8.4 Hz, 1H), 7.02 (d, J=8.4 Hz, 1H), 6.85 (t, J=7.6 Hz, 1H), 6.62 (d, J=7.2 Hz, 1H), 5.26 (s, 2H), 3.96 (t, J=6.0 Hz, 2H), 2.21-2.16 (m, 4H), 1.96 (dd, J=8.0, 15.2 Hz, 1H), 1.83-1.80 (m, 1H), 1.67-1.59 (m, 2H), 1.35-1.31 (m, 1H), 1.28-1.18 (m, 1H), 0.85 (d, J=6.4 Hz, 3H).

Mass Spectrum (ESI) m/e 461.2.

Elemental Analysis: Calculated: C, 58.93%; H, 5.54%; N, 5.50%; S, 3.15. Observed: C, 58.30%; H, 5.36%; N, 5.42%; S, 3.47.

The Compound A hemisulfate form 1 was also obtained according to the same manner as that mentioned above using acetonitrile (18 mL) as a solvent instead of 2-propanol (18 mL).

The elemental analysis of Compound A hemisulfate form 1 shows that it contains a two to one ratio of Compound A cation to sulfate anion.

The presence of the sulfate anion as well as the sulfate stoichiometry was confirmed through elemental analysis, which revealed two molecules of Compound A to one molecule of sulfate anion.

The sulfate salt was named Compound A hemisulfate form 1. This form was subjected to a thermodynamic stability form screen to see if a more stable form could be identified as well as screen for solvates, hydrates, and assess the risk of disproportionation (Example 7). Chemical and physical stability data as well as hygroscopicity data were also generated for Compound A hemisulfate form 1 (Example 11).

Example 6

Compound A Hemisulfate Form 1 Characterization

Physical characterization consisting of XRPD (FIG. 1), TGA, and DSC was performed for Compound A hemisulfate form 1. A summary of the XRPD data from FIG. 1 for Compound A hemisulfate Form 1 is provided in Table 3.

TABLE 3

| Number | Position [°2θ] | d-spacing [Å] | Height [cts] |
|---|---|---|---|
| 1 | 7.2723 | 12.15596 | 203.49 |
| 2 | 8.3321 | 10.61206 | 87.18 |
| 3 | 12.9823 | 6.81943 | 34.79 |
| 4 | 14.682 | 6.03356 | 187.57 |
| 5 | 15.7717 | 5.61908 | 68.85 |
| 6 | 16.5492 | 5.35679 | 72.4 |
| 7 | 17.3066 | 5.12403 | 36.33 |
| 8 | 19.1525 | 4.63415 | 149.22 |
| 9 | 19.6624 | 4.51512 | 80.9 |
| 10 | 20.7187 | 4.28724 | 15.2 |
| 11 | 22.268 | 3.99234 | 224.73 |
| 12 | 23.8209 | 3.73547 | 49.9 |
| 13 | 24.5362 | 3.62817 | 37.27 |
| 14 | 24.9107 | 3.57448 | 34.45 |
| 15 | 25.7712 | 3.45704 | 95.31 |
| 16 | 26.2777 | 3.39155 | 39.15 |
| 17 | 27.8254 | 3.20632 | 40.71 |
| 18 | 28.5033 | 3.13158 | 16 |
| 19 | 29.5617 | 3.02183 | 16.5 |
| 20 | 33.7206 | 2.65804 | 3.18 |

X-ray powder diffraction data were collected under ambient conditions on a Rigaku Miniflex 600 diffractometer using Cu K alpha (1.5406 Angstrom) radiation. Powder patterns were collected on a zero background holder with a 0.1 mm indent at a scan rate of 2 to 400 two theta at 20 per min at 40 kV and 15 mA. Data was analyzed using High Score Plus version 4.1.

Example 7

Compound A Hemisulfate Form Screening

A thermodynamic stability form screen was initiated with Compound A hemisulfate form 1 to screen for thermodynamically more stable polymorphs, solvates, and hydrates as well as to probe the tendency to disproportionate back to Compound A. Approximately 90 to 110 mg of Compound A hemisulfate form 1 was weighed out and transferred into 4 mL amber glass vials followed by 0.8 to 1 mL of solvent and a magnetic stir bar. The vials were sealed then placed onto temperature controlled stir plates and stirred for fifteen days at 500 rpm. Solvents and temperatures are listed in Table 4. XRPD analyses of the solids revealed no change in solid state form occurred except for the solids isolated from experiments in methanol at 25° C. and water/methanol at 25° C. This new form is different than the starting Compound A free form and Compound A hemisulfate form 1.

TABLE 4

Compound A Hemisulfate Slurry Screen

| Experiment | Solvent | Temperature | Results |
|---|---|---|---|
| 1 | Ethyl Acetate | 50° C. | No change in form |
| 2 | 2-Propanol | 50° C. | No change in form |
| 3 | Acetone | 25° C. | No change in form |
| 4 | Dichloromethane | 4° C. | No change in form |
| 5 | Acetonitrile | 50° C. | No change in form |
| 6 | Tetrahydrofuran | 25° C. | No change in form |
| 7 | Water | 25° C. | No change in form |
| 8 | Water/Methanol (1/3, v/v) | 25° C. | Compound A Hemisulfate Form 2 |
| 9 | Water/Acetonitrile (1/3, v/v) | 4° C. | No change in form |

TABLE 4-continued

Compound A Hemisulfate Slurry Screen

| Experiment | Solvent | Temperature | Results |
|---|---|---|---|
| 10 | Ethanol | 50° C. | No change in form |
| 11 | 2-Methyl-THF | 25° C. | No change in form |
| 12 | CPME | 50° C. | No change in form |
| 13 | Toluene | 50° C. | No change in form |
| 14 | Methanol | 25° C. | Compound A Hemisulfate Form 2 |

Example 8

Compound A Hemisulfate Form 2 Characterization

The new solid state form isolated from the methanol slurry and water/methanol slurry in Example 7 was subjected to additional characterization and found to be a new polymorph of the hemisulfate salt of Compound A. This new form was named Compound A hemisulfate form 2. Physical characterization consisting of XRPD (FIG. 2), TGA and DSC was performed for Compound A hemisulfate form 2 after drying under nitrogen. A summary of the XRPD data from FIG. 2 for Compound A hemisulfate form 2 is provided in Table 5.

TABLE 5

| Number | Position [°2θ] | d-spacing [Å] | Height [cts] |
|---|---|---|---|
| 1 | 6.6699 | 13.25246 | 565.65 |
| 2 | 10.0501 | 8.80157 | 17.65 |
| 3 | 11.077 | 7.98776 | 17.71 |
| 4 | 13.5016 | 6.55831 | 54.27 |
| 5 | 14.2386 | 6.22046 | 23.63 |
| 6 | 14.5068 | 6.10605 | 44.53 |
| 7 | 14.8445 | 5.96788 | 22.89 |
| 8 | 16.0872 | 5.50958 | 33.53 |
| 9 | 16.9192 | 5.24047 | 17.12 |
| 10 | 17.4339 | 5.08691 | 84.25 |
| 11 | 18.0914 | 4.90349 | 288.69 |
| 12 | 18.975 | 4.67709 | 26.04 |
| 13 | 19.899 | 4.46195 | 12.96 |
| 14 | 22.3828 | 3.97212 | 48.96 |
| 15 | 23.2046 | 3.83327 | 41.82 |
| 16 | 23.4233 | 3.79797 | 44.01 |
| 17 | 25.0416 | 3.55607 | 29.72 |
| 18 | 26.7503 | 3.33269 | 20.02 |
| 19 | 27.3864 | 3.2567 | 20.05 |
| 20 | 29.3568 | 3.04246 | 9.17 |

X-ray powder diffraction data were collected under ambient conditions on a Rigaku Miniflex 600 diffractometer using Cu K alpha (1.5406 Angstrom) radiation. Powder patterns were collected on a zero background holder with a 0.1 mm indent at a scan rate of 2 to 400 two theta at 2° per min at 40 kV and 15 mA. Data was analyzed using High Score Plus version 4.1.

Solution $^1$HNMR and elemental analysis data were also generated to check for chemical changes, as compared against the free base and initial hemisulfate form 1. The data indicate no molecular transformation occurred and that Compound A hemisulfate form 2 is not a solvate. Also, the solution $^1$H NMR and elemental analysis data were consistent with the material being a hemisulfate salt having a two to one ration of Compound A cation to sulfate anion.

Example 9

Relative Thermodynamic Stability of Compound A Hemisulfate Form 1 and Form 2

The relative thermodynamic stability of Compound A hemisulfate form 1 and hemisulfate form 2 was determined through a comparison of thermal analysis data for each form as well as competition slurry experiments. DSC data for Compound A hemisulfate form 1 revealed this form has an onset melting point of 185.7° C. and an enthalpy of fusion of 106.9 joules per gram. DSC data for Compound A hemisulfate form 2 revealed this form has an onset melting point of 177.4° C. and an enthalpy of fusion of 98.9 joules per gram. According to the heat of fusion rule, Compound A hemisulfate form 1 and hemisulfate form 2 are montropically related given Compound A hemisulfate form 1 has the higher melting point and the higher enthalpy of fusion of the two polymorphs. Compound A hemisulfate form 1 is the thermodynamically more stable form.

Competition slurry experiments were conducted to confirm the relative thermodynamic stabilities of Compound A hemisulfate form 1 and Compound A hemisulfate form 2. Mixtures of both forms were slurried together in 0.5 mL acetone at 25° C. for one week. Both forms were still present in the slurry, so the experiment was moved to 4° C. After ten days at 4° C., XRPD analysis showed that the mixture converted to Compound A hemisulfate form 1, indicating Compound A hemisulfate form 1 is more stable than Compound A hemisulfate form 2 at 4° C.

Compound A hemisulfate form 1 and Compound A hemisulfate form 2 were slurried together in 0.5 mL acetonitrile at 50° C. After three days at 50° C., XRPD analysis showed both forms still remaining in the slurry. After ten days at 50° C. in acetonitrile, XRPD analysis showed that the mixture converted to Compound A hemisulfate form 1, indicating the Compound A hemisulfate form 1 is more thermodynamically stable than Compound A hemisulfate form 2 at 50° C.

Compound A hemisulfate form 1 and Compound A hemisulfate form 2 were slurried together in 0.5 mL ethyl acetate at 25° C. After two days, both forms were still present in the slurry, so the experiment was moved to 4° C. After eight days at 4° C., XRPD analysis showed that the solids remained a mixture of forms. This experiment was stopped before fully converting to a single form given mixtures converted to Compound A hemisulfate form 1 in acetone at 4° C. and in acetonitrile at 50° C. This experiment demonstrates the conversion from Compound A hemisulfate form 2 to Compound A hemisulfate form 1 can be slow under certain conditions.

Both thermal analysis data and competition slurry experiment data demonstrate Compound A hemisulfate form 1 is thermodynamically more stable than Compound A hemisulfate form 2. Methanol was always present in the solvent system when Compound A hemisulfate form 2 was formed which suggests Compound A hemisulfate form 2 might be formed through the desolvation of an unstable and never observed methanol solvate.

Example 10

Compound A Hemisulfate Form 1 Stability and Hygroscopicity

An eight week chemical and physical stability study was conducted for Compound A hemisulfate form 1. The material was stored at 4° C., 25° C./60% RH, 40° C., and 40° C./75% RH for eight weeks as well as stressed conditions of 70° C. and 70° C./75% RH for two weeks. In addition, photostability was also measured after exposing the material to two cycles of ICH conditions. Degradation and recovery was measured by HPLC. See Table 6 for HPLC results, including percent recovery of solids and relative retention time area percentages, compared against the standard stored at 4° C.

TABLE 6

Summary of HPLC data.

| Sample | % | RRT | *RRT | RRT | RRT | RRT | RRT | RRT |
|---|---|---|---|---|---|---|---|---|
| 4° C., 4 wk | 101 | 1.16 | 0.21 | 97.36 | 0.21 | 0.20 | 0.25 | 0.58 |
| 4° C., 8 wk | 100 | 1.15 | 0.12 | 97.42 | 0.34 | 0.19 | 0.24 | 0.54 |
| 25° C./60% RH, 4 wk | 100 | 1.20 | 0.21 | 97.40 | 0.21 | 0.21 | 0.25 | 0.50 |
| 25° C./60% RH, 8 wk | 99 | 1.15 | 0.04 | 97.67 | 0.25 | 0.19 | 0.23 | 0.46 |
| 40° C., 4 wk | 101 | 1.20 | 0.22 | 97.27 | 0.21 | 0.20 | 0.25 | 0.59 |
| 40° C., 8 wk | 101 | 1.16 | 0.11 | 97.44 | 0.33 | 0.19 | 0.24 | 0.53 |
| 40° C./75% RH, 4 wk | 101 | 1.24 | 0.21 | 97.33 | 0.21 | 0.21 | 0.25 | 0.50 |
| 40° C./75% RH, 8 wk | 100 | 1.19 | 0.04 | 97.63 | 0.30 | 0.19 | 0.23 | 0.42 |
| 70° C., 2 wk | 101 | 1.20 | 0.18 | 97.34 | 0.22 | 0.21 | 0.26 | 0.55 |
| 70° C./75% RH, 2 wk | 101 | 1.22 | 0.19 | 97.45 | 0.22 | 0.21 | 0.24 | 0.42 |
| Photo | 98 | 1.11 | 0.10 | 97.78 | 0.27 | 0.20 | 0.14 | 0.40 |
| Control (dark) | 100 | 1.16 | 0.07 | 97.53 | 0.30 | 0.19 | 0.23 | 0.53 |
| Standard | N/A | 1.18 | 0.14 | 97.38 | 0.37 | 0.18 | 0.23 | 0.53 |

XRPD was used to check the physical stability. No changes in solid state form were observed in all conditions.

Dynamic vapor sorption analysis was performed on Compound A hemisulfate form 1 at 25° C. At approximately 90% RH, the material reversibly picks up approximately 3.5% water by weight. After DVS was completed, the solid collected was checked by XRPD, which showed that the material remained Compound A hemisulfate form 1.

Example 11

Preparation of Meglumine Salt of Compound B

Two separate methods were used to generate a meglumine salt of Compound B.
Method 1

Compound B (102.7 mg) was combined with meglumine (43.7 mg) and 2 mL of 2-propanol in a 4 mL glass vial. The vial was sealed with a cap and the contents were subjected to sonication at 25° C. for 20 minutes followed by stirring at 50° C. for 60 minutes. The vial was then moved to a new stir plate and the slurry in the vial was stirred at 25° C.
Method 2

Compound B (102.2 mg) was combined with meglumine (43.2 mg) and 2 mL of acetonitrile in a 4 mL glass vial. The vial was sealed with a cap and the contents were subjected to sonication at 25° C. for 20 minutes followed by stirring at 50° C. for 60 minutes. The vial was then moved to a new stir plate and the slurry in the vial was stirred at 25° C.

For both method 1 and method 2, after 2 days of stirring at 25° C., both samples were centrifuged, supernatants discarded, and solids were air dried.

Example 12

Preparation of Hydrate of Meglumine Salt of Compound B

In a 500 mL round bottom flask, a stirred solution of Compound B (20 g, 43.33 mmol) in THF (100 mL) and water (100 mL) was treated meglumine (8.45 g, 43.33 mmol) at 0° C. The resulting reaction mixture was stirred at RT for 6 h. The reaction mixture was concentrated under reduced pressure and solid obtained was dried under reduced pressure (3 h) to afford the title compound as a white solid (28.5 g, 98.95%).

$^1$H NMR (400 MHz, CD$_3$OD): δ 8.75 (s, 1H), 8.02 (d, J=8.4 Hz, 1H), 7.82 (d, J=8.0 Hz 1H), 7.26 (t, J=8.4 Hz, 1H), 7.03 (s, 1H), 6.99 (d, J=8 Hz, 1H), 6.85 (t, J=7.6 Hz, 1H), 6.50 (d, J=7.6 Hz, 1H), 5.25 (s, 2H), 4.09-3.99 (m, 3H), 3.97-3.77 (m, 2H), 3.74-3.61 (m, 3H), 3.29-3.06 (m, 2H), 2.64 (s, 3H), 2.22 (s, 3H), 2.18-2.14 (m, 1H), 1.99-1.94 (m, 2H), 1.83-1.75 (m, 2H), 1.51-1.38 (m, 1H), 1.32-1.22 (m, 1H), 0.86 (d, J=6.0 Hz, 3H).

$^{19}$F NMR (400 MHz, CD$_3$OD): δ −69.39.

Elemental Analysis: Calcd for $C_{31}H_{43}F_3N_4O_8 \cdot H_2O$: C, 55.18; H, 6.72; N, 8.30. Found: C, 54.95; H, 6.89; N, 8.07.

Moisture Content (Karl Fischer): 2.33%

The elemental analysis of Compound B meglumine salt shows that it contains a one to one to ratio of Compound A cation to meglumine anion to water molecule.

What is claimed is:

1. A compound of Formula (II):

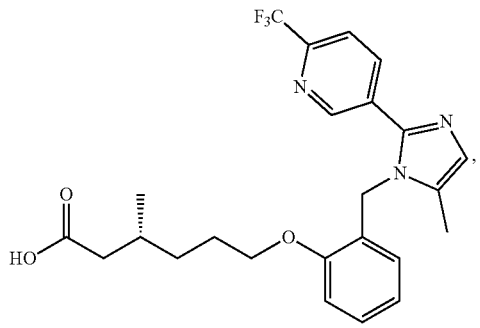

Formula (II)

in the form of a meglumine salt or a hydrate of the meglumine salt.

2. The compound of claim 1, wherein the compound is in the form of a monohydrate.

3. The compound of claim 1, wherein the compound is unhydrated.

4. A pharmaceutical composition comprising the compound of claim 1, and a pharmaceutically acceptable excipient.

5. A method of treating a PPARδ related disease or condition in a subject, comprising administering to the subject in need thereof a therapeutically effective amount of the compound of claim 1.

6. The method of claim 5, wherein the PPARδ related disease is a muscle structure disorder, a neuronal activation disorder, a muscle fatigue disorder, a muscle mass disorder, a mitochondrial disease, a beta oxidation disease, a metabolic disease, a cancer, a vascular disease, an ocular vascular disease, a muscular eye disease, or a renal disease.

7. The method of claim 6, wherein:
the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorder, myotonic chondrodystrophy, myotonic dystrophy, myotubular myopathy, nemaline body disease, oculopharyngeal MD, or stress urinary incontinence;
the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, or toxic myoneural disorder;
the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, or thyrotoxic myopathy;
the muscle mass disorder is cachexia, cartilage degeneration, cerebral palsy, compartment syndrome, critical illness myopathy, inclusion body myositis, muscular atrophy (disuse), sarcopenia, steroid myopathy, or systemic lupus erythematosus;
the mitochondrial disease is selected from Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, or Pearson Syndrome;
the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency or a riboflavin-responsive disorder of β-oxidation (RR-MADD);
the metabolic disease is selected from hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenoleukodystrophy, dermatitis, psoriasis, acne, skin aging, trichosis, inflammation, arthritis, asthma, hypersensitive intestine syndrome, ulcerative colitis, Crohn's disease, or pancreatitis;
the cancer is a cancer of the colon, large intestine, skin, breast, prostate, ovary, or lung;
the vascular disease is selected from peripheral vascular insufficiency, peripheral vascular disease, intermittent claudication, peripheral vascular disease (PVD), peripheral artery disease (PAD), peripheral artery occlusive disease (PAOD), or peripheral obliterative arteriopathy;
the ocular vascular disease is selected from age-related macular degeneration (AMD), stargardt disease, hypertensive retinopathy, diabetic retinopathy, retinopathy, macular degeneration, retinal haemorrhage, or glaucoma;
the muscular eye disease is selected from strabismus, progressive external ophthalmoplegia, esotropia, exotropia, a disorder of refraction and accommodation, hypermetropia, myopia, astigmatism, anisometropia, presbyopia, a disorder of accommodation, or internal ophthalmoplegia; and
the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute kidney injury, chronic renal failure, diabetic nephropathy, or Bartter's syndrome.

8. A method of treating acute kidney injury in a subject, comprising administering to the subject in need thereof a therapeutically effective amount of a compound of claim 1.

9. A method of treating a mitochondrial disease in a subject, comprising administering to the subject in need thereof a therapeutically effective amount of a compound of claim 1, wherein the mitochondrial disease is Alpers Disease, chronic progressive external ophthalmoplegia (CPEO), Kearns-Sayra Syndrome (KSS), Leber Hereditary Optic Neuropathy (LHON), MELAS-mitochondrial myopathy, encephalomyopathy, lactic acidosis, and stroke-like episodes, myoclonic epilepsy with ragged-red fiber disease (MERRF), neurogenic muscle weakness-ataxia-retinitis pigmentosa (NARP), or Pearson Syndrome.

* * * * *